US009372533B1

(12) United States Patent
Agrama

(10) Patent No.: US 9,372,533 B1
(45) Date of Patent: Jun. 21, 2016

(54) FACIAL MOVEMENT MEASUREMENT AND STIMULATION APPARATUS AND METHOD

(71) Applicant: Mark Agrama, Palm Beach Gardens, FL (US)

(72) Inventor: Mark Agrama, Palm Beach Gardens, FL (US)

(*) Notice: Subject to any disclaimer, the term of this patent is extended or adjusted under 35 U.S.C. 154(b) by 265 days.

(21) Appl. No.: 13/948,612

(22) Filed: Jul. 23, 2013

Related U.S. Application Data

(63) Continuation-in-part of application No. 12/427,739, filed on Apr. 21, 2009, now Pat. No. 8,493,286.

(51) Int. Cl.
*G06F 3/01* (2006.01)
*A61N 1/04* (2006.01)
*A63F 13/20* (2014.01)

(52) U.S. Cl.
CPC .............. *G06F 3/012* (2013.01); *A61N 1/0452* (2013.01); *A63F 13/06* (2013.01)

(58) Field of Classification Search
CPC ........... G06F 3/01; G06F 3/012; G06F 1/163; A61N 1/04; A61N 1/0452; A63F 13/06; A63F 13/10
See application file for complete search history.

(56) References Cited

U.S. PATENT DOCUMENTS

| 6,121,953 | A  | * | 9/2000  | Walker | G06F 3/011 |
|-----------|----|---|---------|--------|------------|
|           |    |   |         |        | 2/421      |
| 6,629,760 | B1 | * | 10/2003 | Razin  | G02C 3/003 |
|           |    |   |         |        | 351/156    |
| 8,149,280 | B2 | * | 4/2012  | Yoda   | H04N 5/23219 |
|           |    |   |         |        | 348/207.1  |
| 8,593,375 | B2 | * | 11/2013 | Maltz  | G06F 3/013 |
|           |    |   |         |        | 345/8      |

* cited by examiner

*Primary Examiner* — Abbas Abdulselam
(74) *Attorney, Agent, or Firm* — Glenn E. Gold; Gold & Rizvi, P.A.

(57) ABSTRACT

An illustrative embodiment of a facial movement measurement and stimulation apparatus includes at least one facial movement sensor adapted to sense facial movement in a subject and a wearable computing device interfacing with the facial movement sensor or sensors and adapted to receive at least one signal from the facial movement sensor or sensors and indicate facial movement of the subject on a display of the wearable computing device. A facial movement measurement and stimulation method utilizing the wearable computing device is also disclosed.

16 Claims, 14 Drawing Sheets

FACIAL MOVEMENT MEASUREMENT AND STIMULATION APPARATUS AND METHOD

CROSS-REFERENCE TO RELATED APPLICATION

This Continuation-In-Part Utility Application claims the benefit of co-pending U.S. Non-Provisional patent application Ser. No. 12/427,739, filed on Apr. 21, 2009, which is incorporated herein in its entirety.

FIELD OF THE INVENTION

The present disclosure generally relates to apparatuses and methods for stimulating and measuring the movement of facial muscles. More particularly, the present disclosure relates to an apparatus and method for stimulating, measuring, and utilizing facial muscle movement data with a wearable computing device.

BACKGROUND OF THE INVENTION

Facial expressions, while displayed by many animal species, are most highly developed in primates and most particularly in humans. Although humans have developed a great capacity to communicate using verbal language, the role of facial expressions in interpersonal interactions remains substantial. Facial expressions provide a means of understanding a person's innermost thoughts and emotions, which may defy interpretation by verbal means alone. Therefore, facial expressions in combination with verbal expressions tend to more accurately convey the intended thoughts, feelings and intentions of a person than can be conveyed through verbal expressions only. Moreover, facial expressions and the underlying emotions of which they are a manifestation tend to be contagious, as a person who sees a smiling person is likely to embrace and reflect the positive emotions of that person by smiling as well.

Restoration of a person's lost ability to properly express his or her thoughts and emotions through facial expressions or training of a person in mimicking facial expressions may be desirable in a variety of contexts. In some cases, the ability of a person to express his or her underlying thoughts and emotions accurately through appropriate facial expressions, or the ability of a person to change facial expressions according to changing thoughts and emotions, may diminish or disappear due to causes such as disease, accident or drug abuse, for example. Additionally, actors-in-training may encounter challenges in reacting to staged situations with appropriate facial expressions, which may be more naturally assumed by persons who encounter the actual situations.

Moreover, computing devices such as personal computers, computer tablets, cellular phones and other handheld computing devices are becoming more prevalent and integral to aspects of modern day living. As such computing devices are rapidly decreasing in size and there is a desire to integrate such computing devices into everyday items in modern living, such as integrating computing capabilities into wearable items.

Therefore, a facial movement measurement and stimulation apparatus for measuring and/or stimulating movement of facial muscles and utilizing such data in wearable computing devices is needed.

SUMMARY OF THE INVENTION

The present disclosure is generally directed to a facial movement measurement and stimulation apparatus and method for measuring and/or stimulating movement of facial muscles in a variety of applications. In some applications, the apparatus and method may determine a person's ability to assume facial expressions by measuring the electrical activity or movement of the person's facial muscles. In some applications, the apparatus and method may be implemented in a therapeutic context in which a person is trained to assume facial expressions that accurately reflect the person's underlying thoughts and emotions or the person is trained to change facial expressions to accurately reflect the person's changing thoughts and emotions. In some applications, the apparatus and method may be used to train a person in mimicking facial expressions in response to staged situations. In some applications, the goals of the apparatus and method may be implemented by facilitating the sharing or transfer of facial expressions between two or more subjects.

In some embodiments, the facial movement measurement and stimulation apparatus may include:

at least one facial movement sensor adapted to sense facial movement in a subject; and a device interfacing with the facial movement sensor and adapted to receive at least one signal from the facial movement sensor and indicate facial movement of the subject.

In another aspect, the at least one facial movement sensor may include at least one electrode.

In still another aspect, the at least one facial movement sensor may include at least one accelerometer.

In yet another aspect, the device may include a video game console.

In a still further aspect, the facial movement sensor or sensors may be provided on a mask.

In another aspect, at least one electrode may interface with the device and the device may be adapted to transmit at least one electrical impulse to the at least one electrode.

In another aspect, one or more low level electrical impulses may, instead of causing firing of the muscles, be provided to cause sensory stimulation as a means for regulating emotions.

In a still further aspect, the at least one facial movement sensor may be provided on a first mask and the at least one electrode may be provided in a second mask.

In yet another aspect, the at least one facial movement sensor may interface with the device through wiring.

In another aspect, the at least one facial movement sensor may interface with the device wirelessly.

In still another aspect, the device may include a computer having a display and the computer may be adapted to indicate facial movement of the subject on the display.

In yet another aspect, the computer may be adapted to present a facial image on the display and present at least one facial movement indication on the facial image.

In another aspect, the at least one facial movement sensor may include a plurality of facial movement sensors.

In still another aspect, the facial expression and the stimulation can be treated as a feedback loop that can be monitored and regulated.

In still another aspect, there is provided a wearable computing system, comprising:

eyeglasses, comprising:
a lens element including a display,
a frame with side arms extending therefrom, and
an eyeglasses body adapted to function as a computing system housing, the computer system housing comprising a computer having a processor, storage, and a wireless communication device; and
at least one sensor adapted to measure facial muscle movement in a user, the at least one sensor in electrical communication with the computer.

In yet another aspect, the at least one sensor is a camera having a camera lens mounted on the eyeglasses such that when the eyeglasses are worn by the user, the camera lens is directed toward the user's face and is configured to capture one at least one of a still image and video of the face, and wherein the processor is configured to receive and compare captured images and video to generate facial movement measurement data therefrom.

In yet another aspect, the at least one sensor is an electrode in electrically conductive communication with a facial muscle of the user and is adapted to transmit an electrical impulse to the facial muscle of the user to electrically stimulate the facial muscle.

In yet another aspect, the wearable computing system further comprises a mask, and the at least one electrode comprises a plurality of electrodes that are carried by the mask.

In another aspect, the mask extends from the eyeglasses.

In another aspect, the plurality of electrodes are located at each of a top portion, a middle portion, and a bottom portion of the face, wherein the top portion, corresponds to the user's forehead area, and wherein the middle portion corresponds to the user's eye and nose area, and wherein the bottom portion corresponds to the user's mouth area.

In another aspect, the at least one electrode comprises a plurality of electrodes mounted on the eyeglasses such that when the eyeglasses are worn by the user, the plurality of electrodes are in electrically conductive communication with the user's facial muscles.

In another aspect, the computer is adapted to output facial muscle movement signals, indicative of facial muscle movement of the user, to the display of the eyeglasses.

In another aspect, the wearable computing system further comprises an instruction set stored in computer storage corresponding to video game software.

In another aspect, the electrical impulse corresponds to a movement of a video game character presented on the display.

In yet another aspect, there is provided a method of measuring and indicating facial movement of a user, comprising steps of providing a wearable computing device having a processor, storage, a user input, and a display; and providing at least one facial movement sensor mounted on the wearable computing device such that the at least on facial movement sensor is directed toward the user's face when the wearable computing system is worn by the user. The wearable computing device receives an input command from the user input commanding the at least one facial movement sensor to transmit an electrical impulse to provide facial movement stimulation to the user's facial muscles. The wearable computing device then transmits the command to the at least one facial movement sensor and receives facial movement measurement data from the at least one facial movement sensor, which data corresponds to nerve-induced electrical stimulation of the user's facial muscles. Furthermore, the wearable computing system can store facial movement measurement data in storage and display an image corresponding to the nerve-induced electrical stimulation of facial muscles on the display of the wearable computing device. Moreover, the wearable computing device may be in the form of one of a group of eyeglasses, a mask, and contact lenses. The facial movement sensor may be a camera having a camera lens directed toward the user's face and the camera can capture at least one of a still image and video of the face. The processor of the computing device can compare the captured images and video of the face and generate facial movement measurement data therefrom. Alternatively, the facial movement sensor can be a plurality of electrodes in electrically conductive communication with facial muscles of the user and the electrodes can transmit an electrical impulse to facial muscles of the user to electrically stimulate the user's facial muscles.

In yet another aspect, there is provided a method of utilizing facial movement data, comprising the steps of providing a wearable computing device adapted to be worn on a user's face and receiving electrical output signals from at least one facial movement sensor mounted on the wearable computing device such that the at least one facial movement sensor is directed toward the user's face when the wearable computing system is worn by the user. The method further includes providing an executable instruction set stored in storage on the wearable computing device, the instruction set providing instructions for a software application adapted to utilize the output signal of the at least one facial movement sensor as a control input; and transmitting the electrical output signals to the software application. An aspect of the software application is controlled in accordance with the electrical output signals from the at least one facial movement sensor. The facial movement sensors can be one of a plurality of electrodes in electrically conductive communication with facial muscles of the user and a camera having a camera lens directed toward the user's face. Furthermore, the method can include providing instructions for a video game and controlling one of an audio component and a video component of the video game in accordance with the electrical output signals.

These and other advantages of the invention will be further understood and appreciated by those skilled in the art by reference to the following written specification, claims and appended drawings.

BRIEF DESCRIPTION OF THE DRAWINGS

The invention will now be described, by way of example, with reference to the accompanying drawings, where like numerals denote like elements and in which.

Like reference numerals refer to like parts throughout the various views of the drawings.

DETAILED DESCRIPTION OF THE INVENTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure which is defined by the claims. Furthermore, there is no intention to be bound by any expressed or implied theory presented in the preceding technical field, background, brief summary or the following detailed description.

The present disclosure is generally directed to a facial movement measurement and stimulation apparatus and method for measuring and/or stimulating movement of facial muscles in a variety of applications. In some applications, the apparatus and method may determine a person's ability to make facial movements or assume facial expressions by measuring the electrical activity or movement of the person's facial muscles. In some applications, the apparatus and method may be implemented in a therapeutic context in which a person is trained to assume facial expressions that accurately reflect the person's underlying thoughts and emotions or the person is trained to change facial expressions to accurately reflect the person's changing thoughts and emotions. Alternatively, the stimulation can be provided at a low enough level to cause sensory stimulation without causing firing of the muscles. In some applications, the apparatus and method may be used to train a person in mimicking facial expressions in response to staged situations. In some applications, the goals of the apparatus and method may be attained by facilitating the sharing or transfer of facial movements or expressions between two or more subjects.

Figure 1:
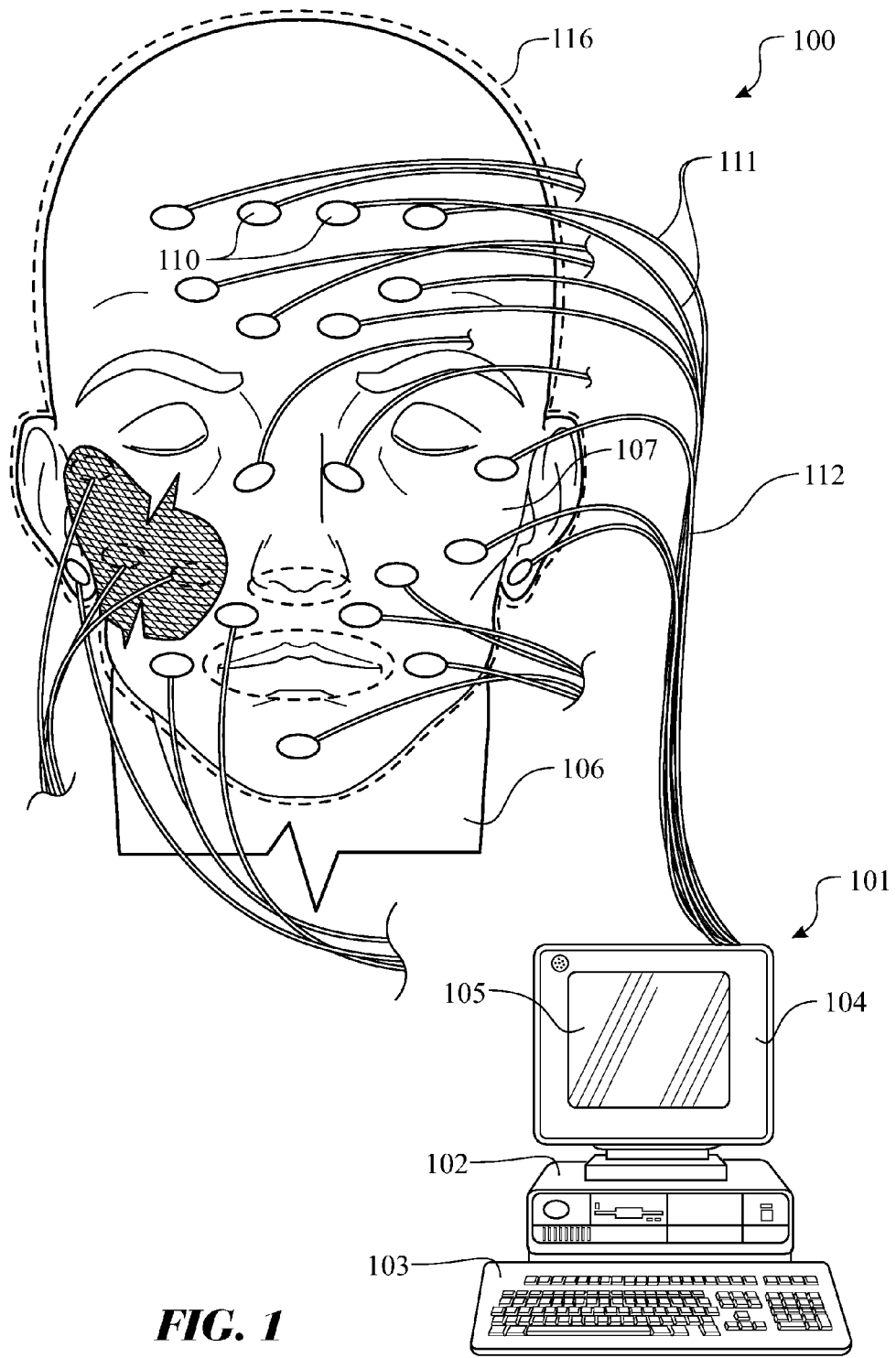
FIG. 1 presents a front view of an illustrative embodiment of the facial movement measurement and stimulation apparatus (partially in section), with multiple electrodes attached to a face of a subject (shown in section) in an implementation of the apparatus.
Figure 2:
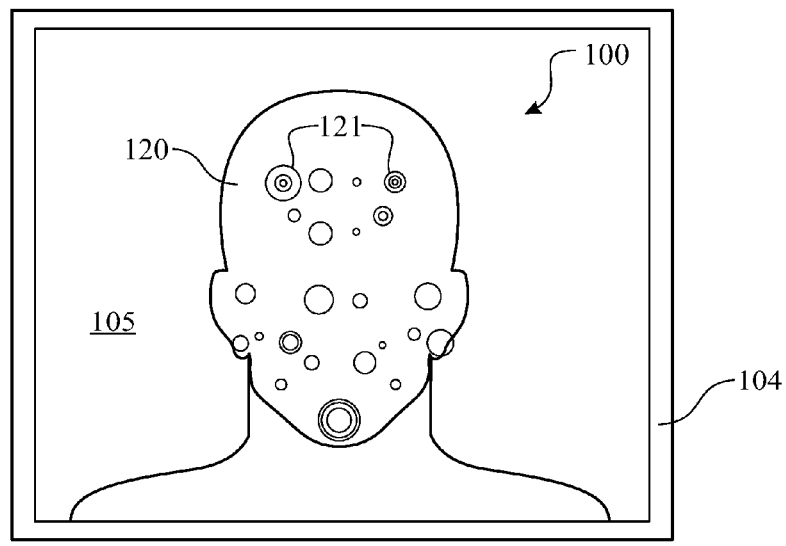
FIG. 2 presents a front view of a computer monitor of an illustrative embodiment of the apparatus, with a facial image of the subject presented on the monitor and multiple facial movement indications presented on the facial image and indicating movement of the subject's facial muscles in the locations that correspond to the facial movement indications.

Referring initially to FIGS. 1 and 2 of the drawings, an illustrative embodiment of the facial movement measurement and stimulation apparatus, hereinafter apparatus, is generally indicated by reference numeral 100 in FIG. 1. In some applications, the apparatus 100 may function as an electromyographic measurement system to measure movements of facial muscles (not illustrated) in the face 107 of a subject 106 for any of a variety of purposes. For example, lack or impairment of movement of the facial muscles in the face 107 of the subject 106, as interpreted by the apparatus 100, may reveal a medical condition (such as facial paralysis due to a stroke, for example) and provide the basis for a medical diagnosis and/or therapeutic treatment regimen for the medical condition. Accordingly, the apparatus 100 may include multiple electrodes 110, which in some applications may function as facial movement sensors that may be placed on the skin (not illustrated) at various locations on the face 107 of the subject 106 to measure movement of the musculature (not illustrated) in the face 107. The locations of the electrodes 100 may correspond in position to individual muscles (not illustrated) of the facial musculature, which underlies the skin in the face 107. In some applications, the electrodes 100 may be confined to a portion of the face 107. In some applications, the electrodes 100 may be placed over the entire face 107 and may additionally or alternatively be placed on one or both ears and/or along the neck and larynx of the subject 106. Each electrode 100 may be adapted to measure both sporadic or continuous high-level electrical nerve stimulation and continuous, low-level electrical nerve stimulation of the muscles in the face 107.

In some embodiments, each electrode 100 may be directly affixed to the face 107 of the subject 106 using a suitable adhesive. In other embodiments, the system 100 may include a flexible or stretchable mask 116, which conforms to the features on the face 107. The electrodes 110 may be provided on a contact surface (not illustrated) of the mask 116 with the skin on the face 107. Adhesive (not illustrated) may be provided on the contact surface of the mask 116 to facilitate adhesion of the mask 116 to the skin on the face 107 and maintain electrically-conductive contact between the electrodes 110 and the skin on the face 107. In some embodiments, the electrodes 110 may be surgically implanted in the skin at the desired locations on the face 107.

The system 100 may further include a computer 101 which in some embodiments may be connected to the electrodes 110 through electrode wiring 111. The electrode wiring 111 may be wrapped in a wiring bundle 112. In other embodiments, the electrodes 110 may interface with the computer 110 through wireless transmissions 130 (FIG. 3), according to the knowledge of those skilled in the art. The computer 101 may be conventional and may include a computer disk drive 102 with a computer keyboard 103 and a computer monitor 104 having a display 105 connected to the computer disk drive 102. In applications in which the electrodes 110 function as facial movement sensors that measure movement of the musculature (not illustrated) in the face 107 of the subject 106, the computer 101 may function as a facial movement measuring and indicating device which receives electrical signals from the electrodes 110 in contact with the face 107. Accordingly, as illustrated in FIG. 2, the computer 101 with supporting software may be programmed to display a facial image 120 on the display 105 of the computer monitor 104. The computer 101 may additionally be programmed to convert the electrical output signals from the electrodes 110 into facial movement indications 121 and present the facial movement indications 121 on the facial image 120 in the areas of the facial image 120 which correspond to areas of muscle movement in the face 107 of the subject 106 in real time as sensed by the electrodes 110.

The strength of the electrical output signals that the computer 101 receives from the electrodes 110 may be proportional to the level or intensity of electrical nerve stimulation and therefore, the level or intensity of contraction of the musculature in the face 107 of the subject 106. Accordingly, the facial movement indications 121 may be adapted to visually differentiate the intensity of muscle movement in each area from the intensity of muscle movement in the other areas in the face 107 of the subject 106. As illustrated in FIG. 2, in some applications each facial movement indication 121 may be represented by one or multiple circles. Facial movement indications 121 having a single circle may indicate muscular contraction of relatively low-level intensity in the corresponding area or areas on the face 107, whereas facial movement indications 121 having multiple concentric circles of increasing number may indicate muscular contraction of correspondingly increasing intensity in the corresponding area or areas on the face 107. The information that is provided by the facial movement indications 121 may be used to formulate diagnoses and/or treatment of the subject 106 or may be used for other purposes.

In some embodiments, the facial movement sensors of the apparatus 100 may be accelerometers instead of the electrodes 110. Accordingly, the accelerometers may be attached to or secured into contact with the skin on the face 107 of the subject 106 or alternatively, surgically implanted in the face 107 in the same manner as was heretofore described with respect to the electrodes 110. The accelerometers sense movement of the muscles in the face 107 of the subject 106 and convert the movement of the muscles into electrical output signals that are transmitted to the computer 101 through the electrode wiring 111. The computer 101 may convert the electrical output signals into the facial movement indications 121, which may be presented on the facial image 120 displayed on the display 105 of the computer monitor 104.

In some applications, the apparatus 100 may electrically stimulate movement of muscles in the face 107 of the subject 106 for any of a variety of purposes. For example, the apparatus 100 may be used in therapeutic applications to enable or train the subject 106 to make facial movements or to assume facial expressions that accurately reflect the person's underlying thoughts and emotions, for example. In some therapeutic applications, the apparatus 100 may be used to train the subject 106 in changing facial expressions to accurately reflect the person's changing thoughts and emotions, for example. In some therapeutic applications, the apparatus 100 may be used to provide a low level stimulus, which causes sensory stimulation for regulation of emotions without causing firing of the muscles. In some therapeutic applications, the apparatus 100 may be used for clinical treatment of headaches, depression, anxiety and the like. In some applications, the apparatus 100 may be used to train a person in accurately mimicking or portraying facial expressions in response to staged situations as in the training of an actor, for example. Accordingly, in these applications the electrodes 110 may be placed on the face 107 of the subject 106 as was heretofore described with respect to the muscle movement measurement functions of the apparatus 100. The computer 101 with supporting software may function as an electrical input device which may be programmed to transmit electrical impulses to the electrodes 110 through the electrode wiring 111 in such a pattern and with such an intensity as to electrically stimulate and contract the musculature in the face 107 and induce the desired facial movements or expressions in the face 107 of the subject 106. In some applications, the computer 101 may be programmed to effect changing facial expressions in the face 107 of the subject 106 by changing the pattern and intensity of the electrical impulses that are transmitted to the electrodes 110.

Figure 3:
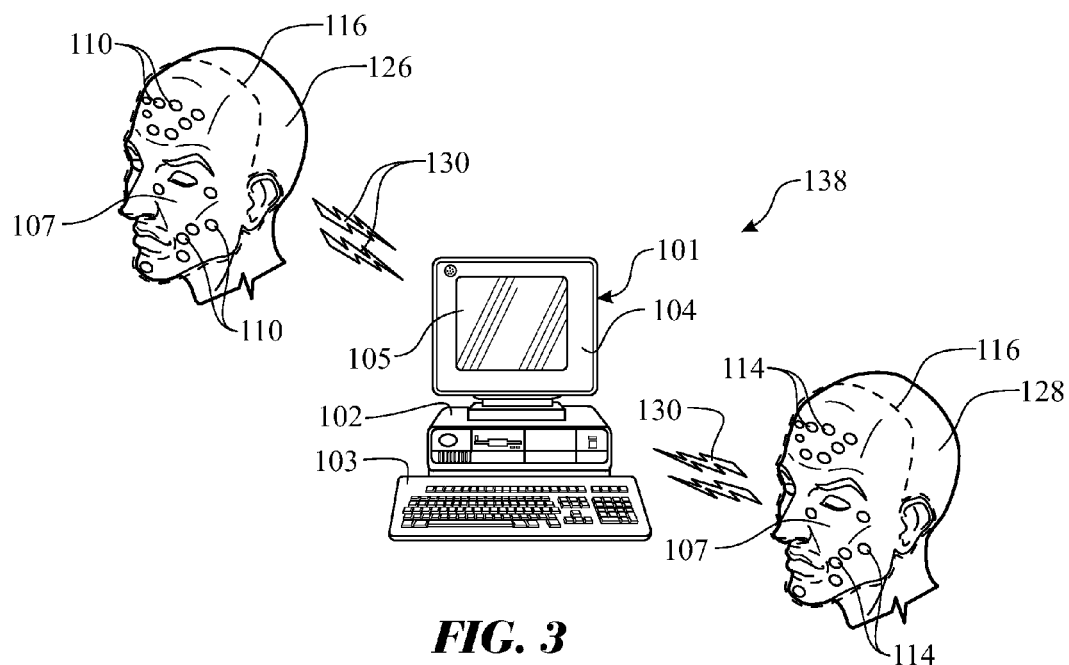
FIG. 3 illustrates implementation of an illustrative embodiment of the apparatus, in which facial movements are transferred or shared between two subjects via wireless communication with a computer.

Referring next to FIG. 3 of the drawings, an alternative illustrative embodiment of the facial movement measurement and stimulation apparatus is generally indicated by reference numeral 138. The apparatus 138 may be adapted to transfer voluntary or involuntary facial movements or expressions from a first subject 126 to a second subject 128 in any of a variety of applications. For example, in some applications the apparatus 138 may transfer voluntary facial movements or expressions from the first subject 126, who may be an acting trainer, to the second subject 128, who may be an actor-in-training. In such applications, the first subject 126 may use the apparatus 138 to train the second subject 128 to accurately mimic or portray facial expressions in response to various staged situations such as those which may occur during dramatic productions, for example. In some applications, the apparatus 138 may be used to facilitate the sharing of emotions between the first subject 126 and the second subject 128 via facial expressions.

The apparatus 138 may include a first set of electrodes 110 for placement on or surgical implantation in the face 107 of the first subject 126 and a second set of electrodes 114 for placement on or surgical implantation in the same corresponding areas on the face 107 of the second subject 128, either with or without the mask 116 as was heretofore described with respect to FIG. 1. The first set of electrodes 110 may function as facial movement sensors which sense movement of the various muscles in the face 107 of the first subject 126 via typically voluntary nerve-induced electrical stimulation of the facial muscles. In some embodiments, the facial movement sensors may be a set of accelerometers which are applied instead of the first set of electrodes 110 to the face 107 of the first subject 126 and which sense movement of the facial muscles. The second set of electrodes 114 may electrically stimulate movement of the various muscles in the face 107 of the second subject 128 according to the intensities and locations of the muscle movements in the face 107 of the first subject 126. Therefore, the computer 101 with supporting software may function as a stimulus transfer device which transfers the muscle movements in the face 107 of the first subject 126, received via the first set of electrodes 110, to the muscles in the face 107 of the second subject 128 via the second set of electrodes 114. In some embodiments, the first set of electrodes 110 and the second set of electrodes 114 may interface with the computer 101 via electrode wiring 111, as was heretofore described with respect to the apparatus 100 in FIG. 1. In other embodiments, the first set of electrodes 110 and the second set of electrodes 114 may interface with the computer 101 via wireless transmissions 130, as illustrated in FIG. 3, according to the knowledge of those skilled in the art.

The computer 101 with supporting software is adapted to receive electrical signals that correspond to typically voluntary, nerve-induced electrical stimulation of the musculature in the face 107 of the first subject 126 through the first set of electrodes 110. The computer 101 may be programmed to determine the locations and intensities of the electrical signals from the electrodes 110 on the various areas on the face 107 of the first subject 126 and transfer electrical impulses which correspond to the electrical signals to the second set of electrodes 114 which are applied to the corresponding areas on the face 107 of the second subject 128. The locations and intensities of the electrical impulses that are transmitted to the second set of electrodes 114 correspond to the locations and intensities of the electrical signals which were received from the first set of electrodes 110. Therefore, the electrical impulses which the second set of electrodes 114 applies to the muscles in the face 107 of the second subject 128 cause contraction of the respective facial muscles to effect the corresponding facial movements or expressions in the second subject 128 that were made by the first subject 126 as the first set of electrodes 110 transmitted the electrical signals to the computer 101. In some embodiments, the locations and intensities of the muscle movements in the face 107 of the first subject 126 may be indicated on the display 105 of the computer 101 such as in the form of the facial movement indications 121, as was heretofore described with respect to FIG. 2.

Figure 4:
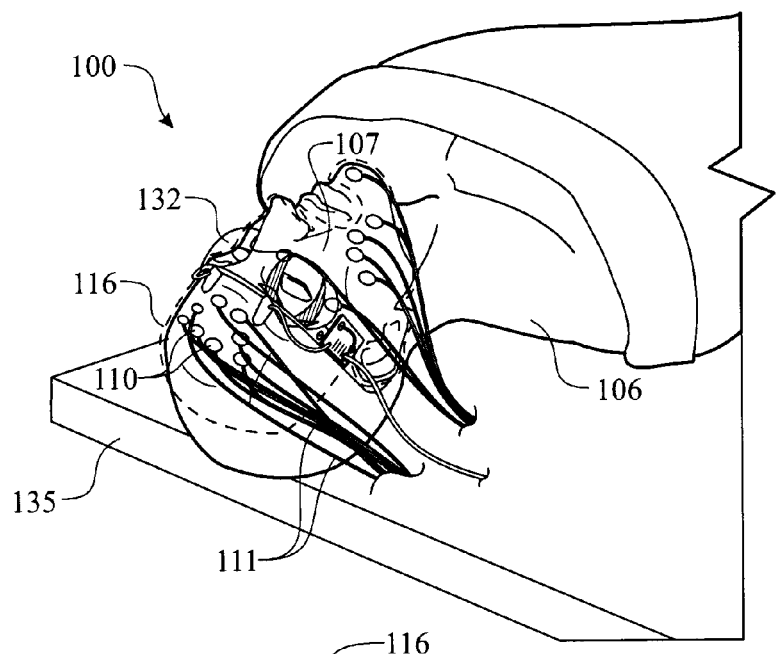
FIG. 4 presents a perspective view of a subject lying on a support (partially in section), with multiple electrodes of an illustrative embodiment of the apparatus attached to the face of the subject and oculography glasses worn by the subject to monitor sleep phases.

Referring next to FIG. 4 of the drawings, in an alternative application of the apparatus 100, which was heretofore described with respect to FIGS. 1 and 2, the electrodes 110 may be applied to the face 107 of a subject 106 as the subject 106 lies on a bed or other support 135. Oculography glasses 132 may be placed on the head of the subject 106 to record eye position and movements of the subject 106 such as in the analysis of various stages of sleep in the subject 106, for example. The stages of sleep can include both non-REM (Rapid Eye Movements) and REM sleep periods. Criteria for REM sleep include not only rapid eye movements, but also low muscle tone and a rapid, low voltage EEG. These features are easily discernible in a polysomnogram, the sleep study typically done for patients with suspected sleep disorders. Accordingly, in use of the apparatus 100, such as during sleep studies conducted on the subject 106, the computer 101 (FIG. 1) may function as a facial movement measuring and indicating device which receives from the electrodes 110 electrical signals that correspond to nerve-induced stimulation of the muscles in the face 107 of the subject 106 either through the electrode wiring 111, as shown, or via wireless transmissions 130 as was heretofore described with respect to FIG. 3. As was heretofore described with respect to FIG. 2, the computer 101 may be programmed to display a facial image 120 on the display 105 of the computer monitor 104 and present facial movement indications 121 on the areas of the facial image 120 which correspond to areas of muscle movement in the face 107 of the subject 106 in real time as sensed by the electrodes 110, as was heretofore described with respect to FIG. 1. The information that is revealed by the facial movement indications 121 on the facial image 120 and by the data received from the oculography glasses 132 may be used for diagnostic, therapeutic and/or other purposes. Additionally or alternatively, the computer 101 may be programmed to electrically stimulate the muscles in the face 107 of the subject 106 via the electrodes 110 for diagnostic, therapeutic and/or other purposes, as was heretofore described.

Figure 5:
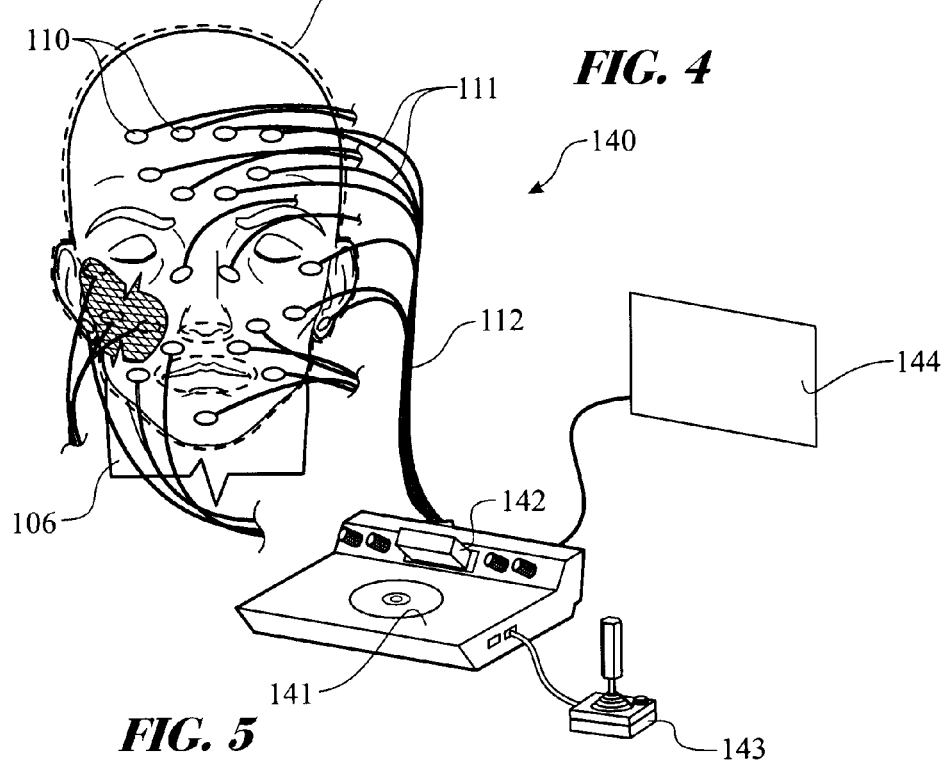
FIG. 5 presents a front view of an alternative illustrative embodiment of the apparatus (partially in section), with multiple electrodes attached to a face of a subject (shown in section) and the electrodes connected to a video game in implementation of the apparatus.

Referring next to FIG. 5 of the drawings, an alternative illustrative embodiment of the facial movement measurement and stimulation apparatus is generally indicated by reference numeral 140. The apparatus 140 may include a video game console 141 which may be adapted to receive one of various types of video game cartridges 142 for the playing of video games on a display 144 connected to the video game console 141. A joystick 143 may be connected to the video game console 142 to facilitate the movement of video game characters (not illustrated) on the display 144 as the video game is played. Electrodes 110 may interface with the video game console 141 via electrode wiring 111, as illustrated in FIG. 5, or alternatively, via wireless transmissions 130 (FIG. 3). The electrodes 110 are adapted for placement at various areas on the face 107 of a subject 106 either with or without the mask 116.

In some applications, the electrodes 110 may function as facial movement sensors which are adapted to sense facial movements or expressions of the subject 106 by measuring typically voluntary, nerve-induced electrical stimulation of the various muscles in the face 107 of the subject 106. The electrodes 110 may transmit electrical signals that correspond to the locations and intensities of the typically voluntary nerve-induced electrical stimulation of the facial muscles of the subject 106 to the video game console 141. The video game console 141 may be adapted to utilize the electrical signals from the electrodes 110 as audio components and/or as visual components of a video game on the display 144 as the video game is played by the subject 106 or by another. The facial movements or expressions of the subject 106 may be used to control one or more aspects or characters of the video game. In some applications, the video game console 141 may be adapted to transfer electrical impulses to the electrodes 110 to effect various facial movements in the face 107 of the subject 106 via electrical stimulation of the facial muscles. The facial movements which are induced in the face 107 of the subject 106 via the electrical impulses may correspond to facial or other movements which are made by a character presented on the display 144 as a video game is being played.

Figure 6:
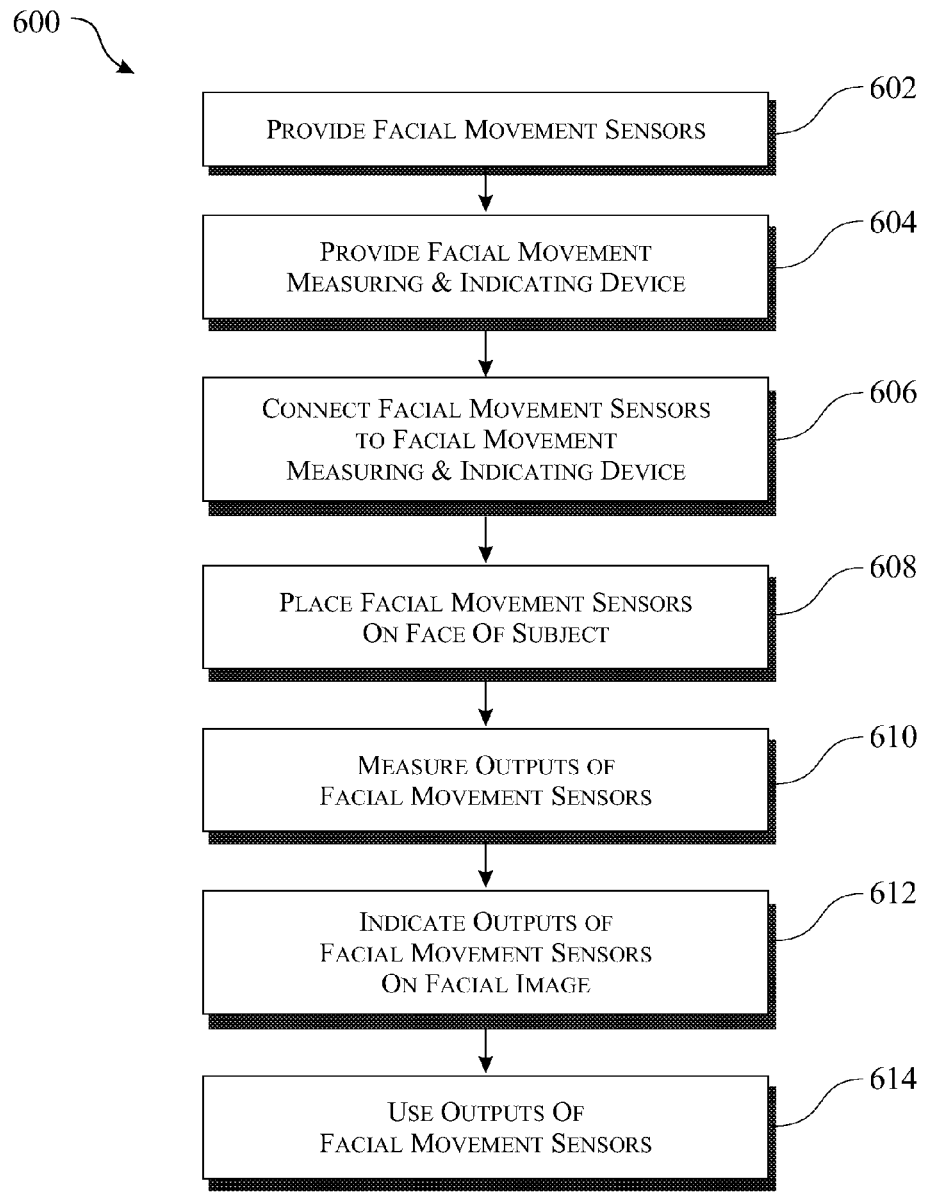
FIG. 6 presents a flow diagram of an illustrative embodiment of a facial movement measurement method in which facial movements of a subject are measured.

Referring next to FIG. 6 of the drawings, a flow diagram of an illustrative embodiment of a facial movement measurement method is generally indicated by reference numeral 600. In block 602, facial movement sensors are provided. In some applications, the facial movement sensors may be electrodes. In some applications, the facial movement sensors may be accelerometers. In block 604, a facial movement measuring and indicating device is provided. In block 606, the facial movement sensors are connected to the facial movement measuring and indicating device. In block 608, the facial movement sensors are placed on or surgically implanted in the face of a subject. In block 610, outputs of the facial movement sensors in the form of electrical signals are measured. In block 612, the outputs of the facial movement sensors may be indicated on a facial image in the form of facial movement indications provided on a display. In block 614, the outputs of the facial movement sensors may be used for diagnostic, therapeutic and/or other purposes.

Figure 7:
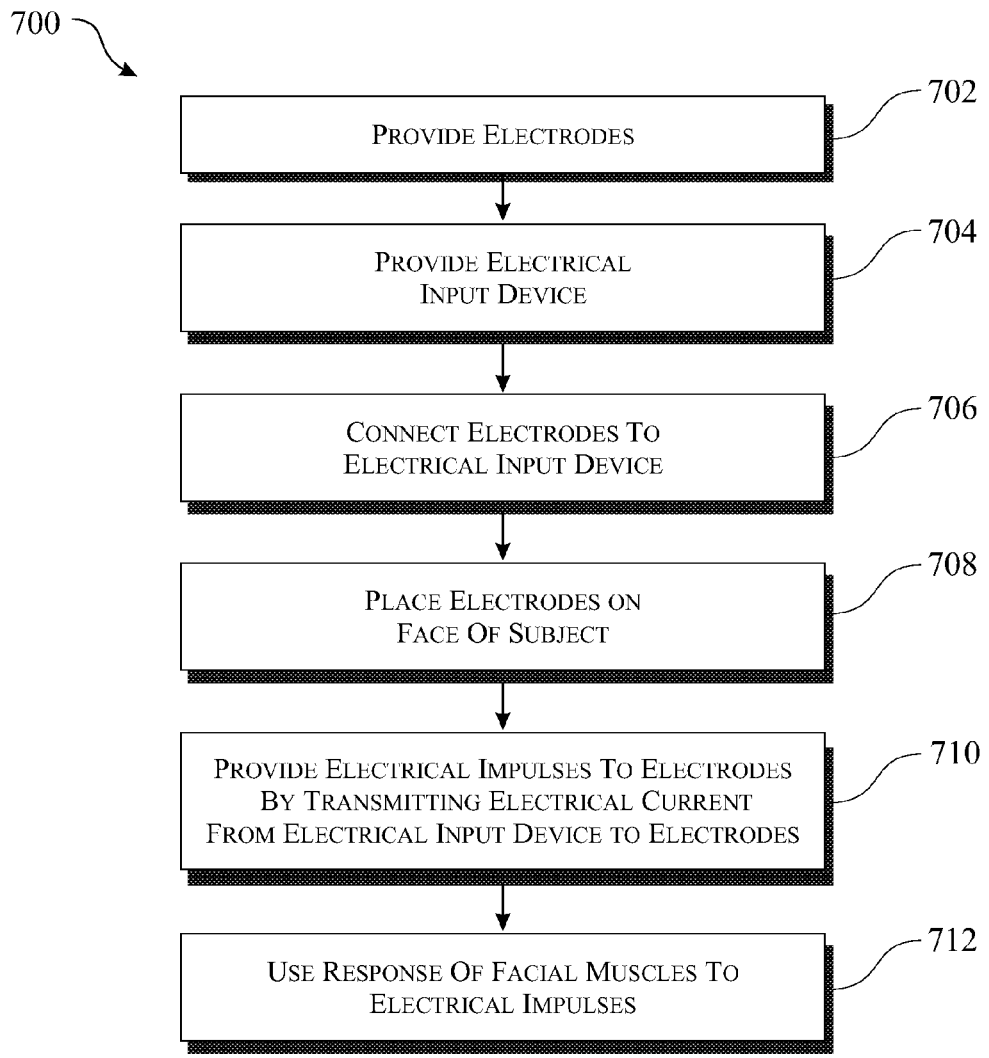
FIG. 7 presents a flow diagram of an illustrative embodiment of a facial movement stimulation method in which facial movements are stimulated in a subject.

Referring next to FIG. 7 of the drawings, a flow diagram of an illustrative embodiment of a facial movement stimulation method is generally indicated by reference numeral 700. In block 702, electrodes are provided. In block 704, an electrical input device is provided. In block 706, the electrodes are connected to the electrical input device. In block 708, the electrodes are placed on or surgically implanted in the face of a subject. In block 710, electrical impulses are provided to the electrodes by transmitting an electrical current from the electrical input device to the electrodes. In block 712, the response of the facial muscles of the subject to the electrical impulses may be used for diagnostic, therapeutic and/or other purposes.

Figure 8:
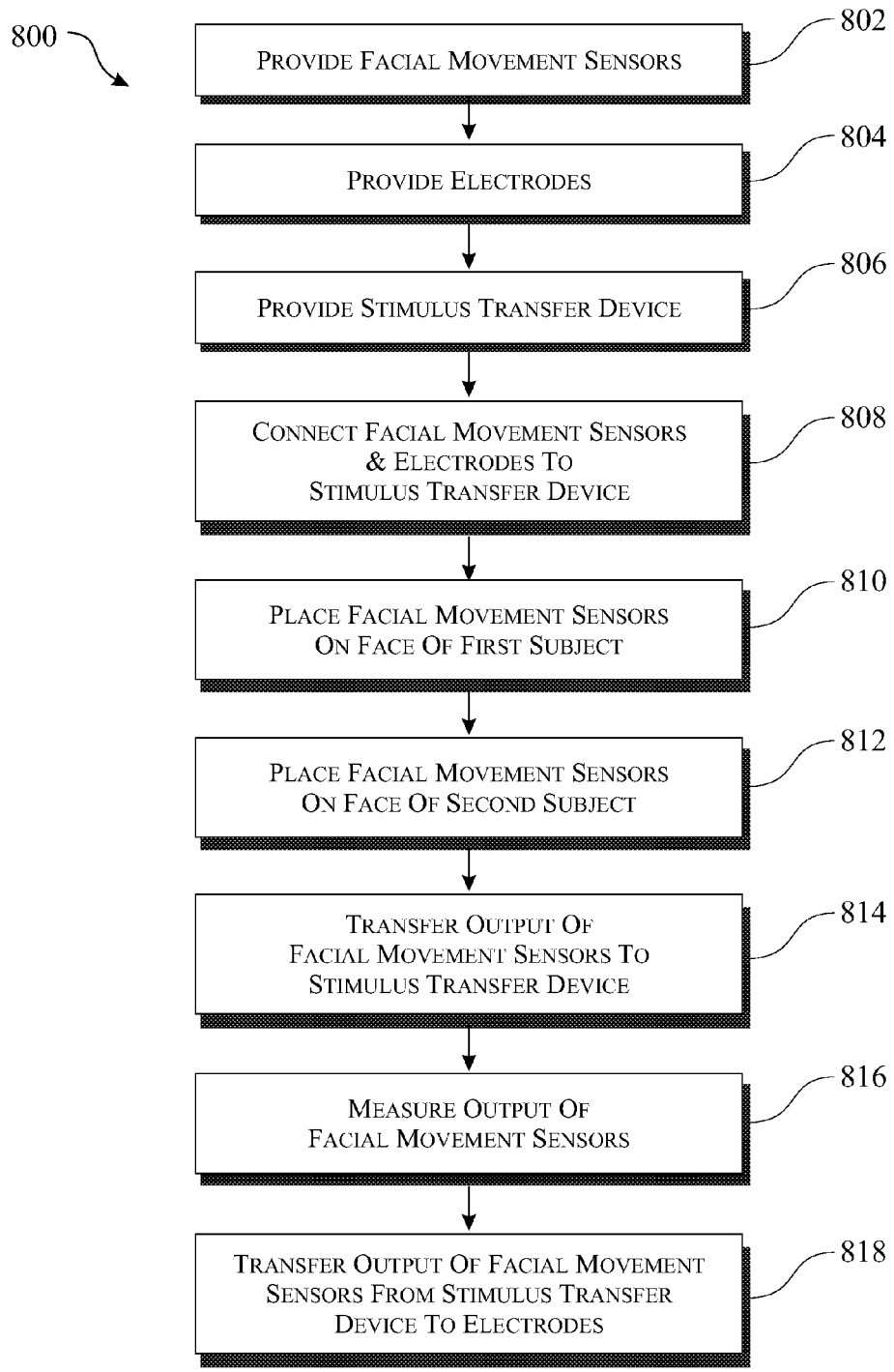
FIG. 8 presents a flow diagram of an illustrative embodiment of a facial movement stimulation method in which facial movements are transferred from a first subject to a second subject.

Referring next to FIG. 8 of the drawings, a flow diagram of an illustrative embodiment of a facial movement stimulation method in which facial movements or expressions are transferred from a first subject to a second subject is generally indicated by reference numeral 800. In block 802, facial movement sensors are provided. In some applications, the facial movement sensors may be electrodes. In some applications, the facial movement sensors may be accelerometers. In block 804, electrodes are provided. In block 806, a stimulus transfer device is provided. In block 808, the facial movement sensors and the electrodes are connected to the stimulus transfer device. In block 810, the facial movement sensors are placed on or surgically implanted in the face of a first subject. In block 812, the electrodes are placed on or surgically implanted in the face of a second subject. In block 814, the output of the facial movement sensors, which may be in the form of electrical signals, is transferred to the stimulus transfer device. In block 816, the output of the facial movement sensors may be measured. In block 818, the output of the facial movement sensors may be transferred from the stimulus transfer device to the electrodes in the form of electrical impulses to effect the same facial movements or expressions in the second subject, as were made by the first subject.

Figure 9:
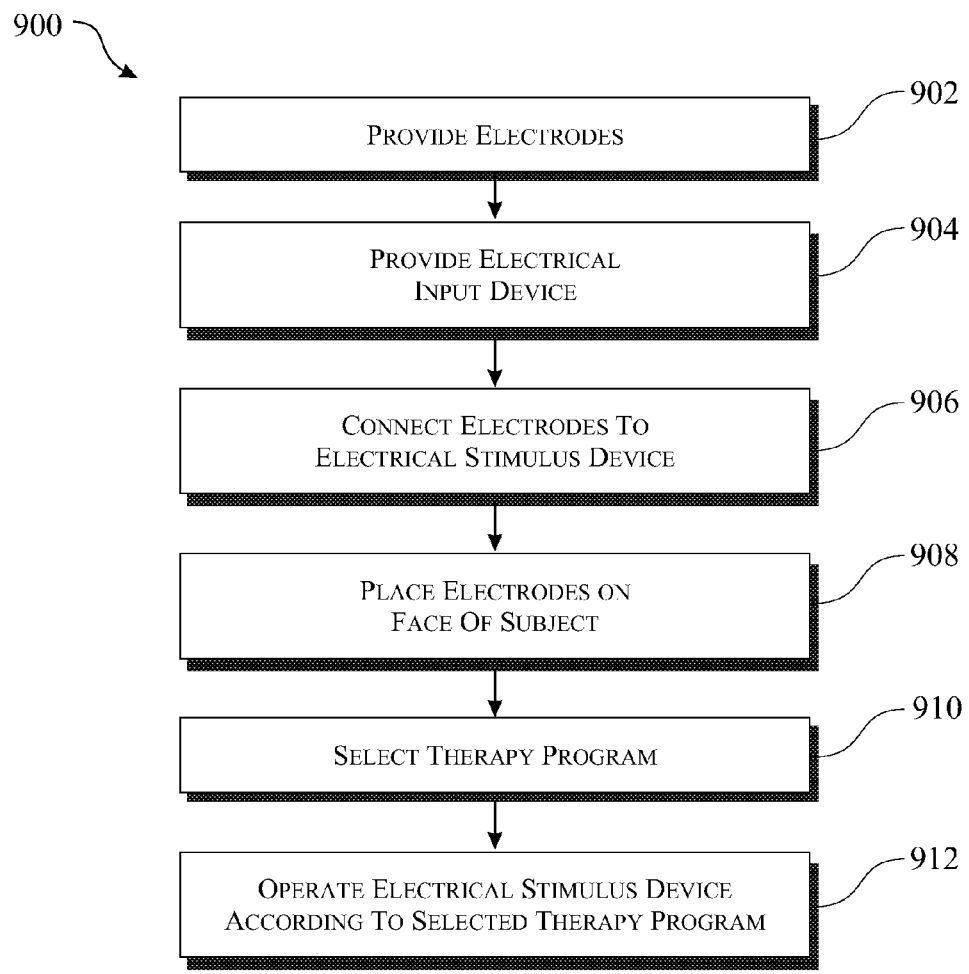
FIG. 9 presents a flow diagram of an illustrative embodiment of a therapeutic facial movement stimulation method.

Referring next to FIG. 9 of the drawings, a flow diagram of an illustrative embodiment of a therapeutic facial movement stimulation method is generally indicated by reference numeral 900. In block 902, electrodes are provided. In block 904, an electrical stimulus device is provided. In block 906, the electrodes are connected to the electrical stimulus device. In block 908, the electrodes are placed on or surgically implanted in the face of a subject. In block 910, a therapy program is selected. In block 912, the electrical stimulus device is operated according to the selected therapy program to induce facial movements or expressions in the subject for therapeutic purposes. In some applications, the selected therapy program may be preprogrammed into a computer which may then automatically cycle through the electrical stimuli induced in the face of the subject to implement the therapy.

Figure 10:
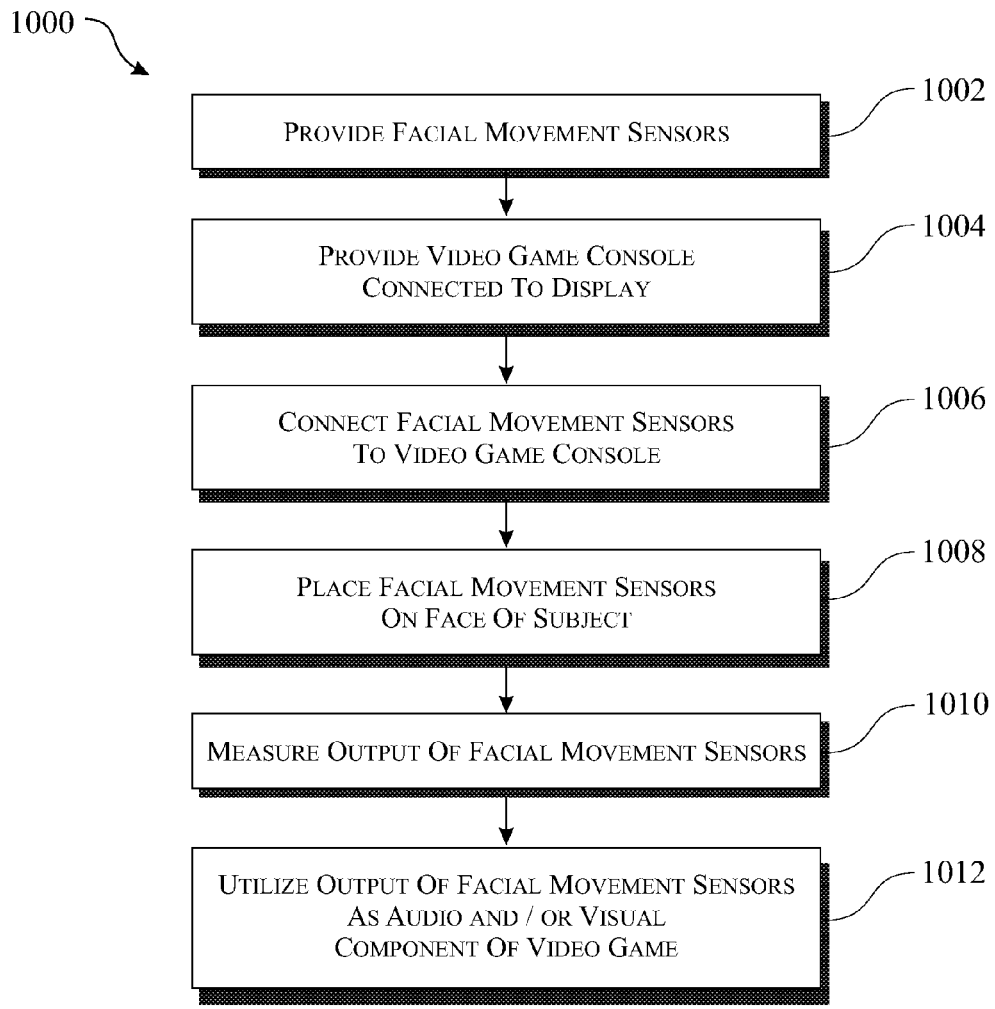
FIG. 10 presents a flow diagram of an illustrative embodiment of a facial movement measurement method in which facial movements of a subject are utilized in a video game.

Referring next to FIG. 10, a flow diagram of an illustrative embodiment of a facial movement measurement method in which facial movements of a subject are utilized in a video game is generally indicated by reference numeral 1000. In block 1002, facial movement sensors are provided. In some applications, the facial movement sensors may be electrodes. In some applications, the facial movement sensors may be accelerometers. In block 1004, a video game console connected to a display is provided. In block 1006, the facial movement sensors are connected to the video game console. In block 1008, the facial movement sensors are placed on or surgically implanted in the face of a subject. In block 1010, the output of the facial movement sensors may be measured. In block 1012, the output of the facial movement sensors may be utilized as an audio and/or visual component of a video game that is played using the video game console.

Figure 11:
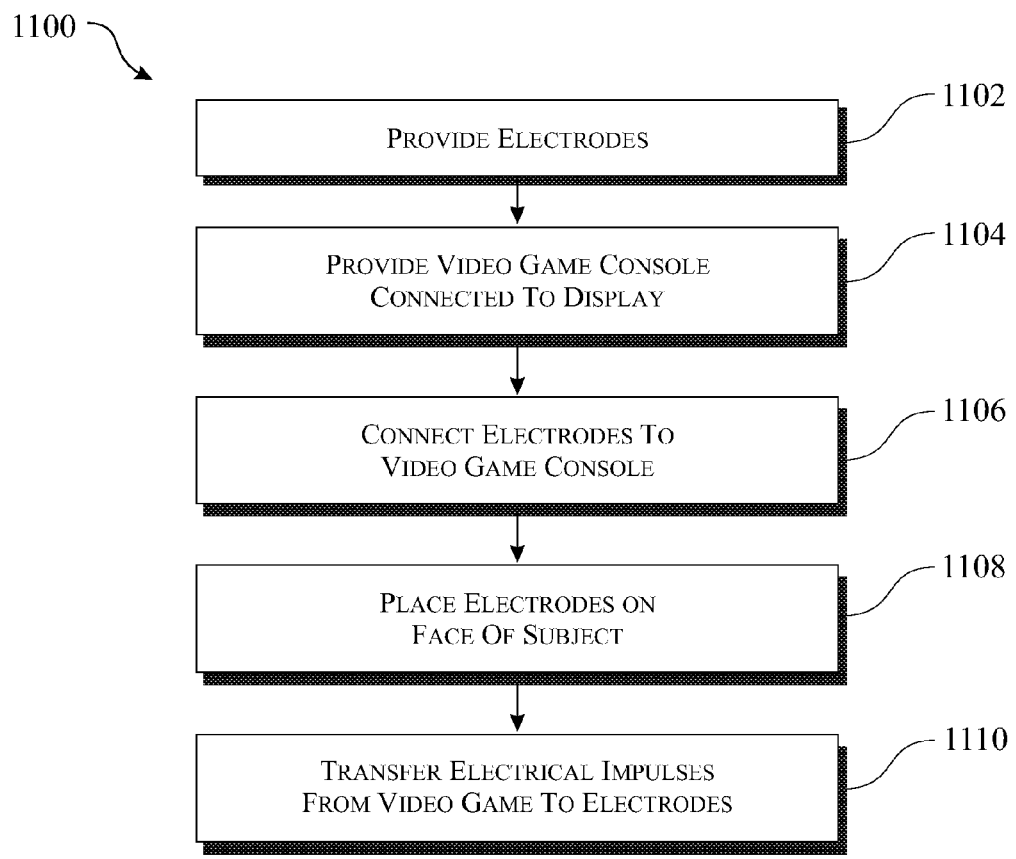
FIG. 11 presents a flow diagram of an illustrative embodiment of the facial movement stimulation method in which electrical stimuli from a video game are transferred to a subject to effect facial movements in the subject.

Referring next to FIG. 11, a flow diagram of an illustrative embodiment of the facial movement stimulation method in which electrical stimuli from a video game are transferred to a subject to effect facial movements in the subject is generally indicated by reference numeral 1100. In block 1102, electrodes are provided. In block 1104, a video game console connected to a display is provided. In block 1106, the electrodes are connected to the video game console. In block 1108, the electrodes are placed on or surgically implanted in the face of a subject. In block 1110, electrical impulses are transferred from the video game console to the electrodes to induce facial movements or expressions in the subject. The facial movements or expressions which are induced in the face of the subject may correspond to facial or other movements or expressions which are made by a character presented on the display as a video game is being played using the video game console. In some applications, the facial movements or expressions of the subject may be used to control one or more aspects of the video game.

Figure 12:
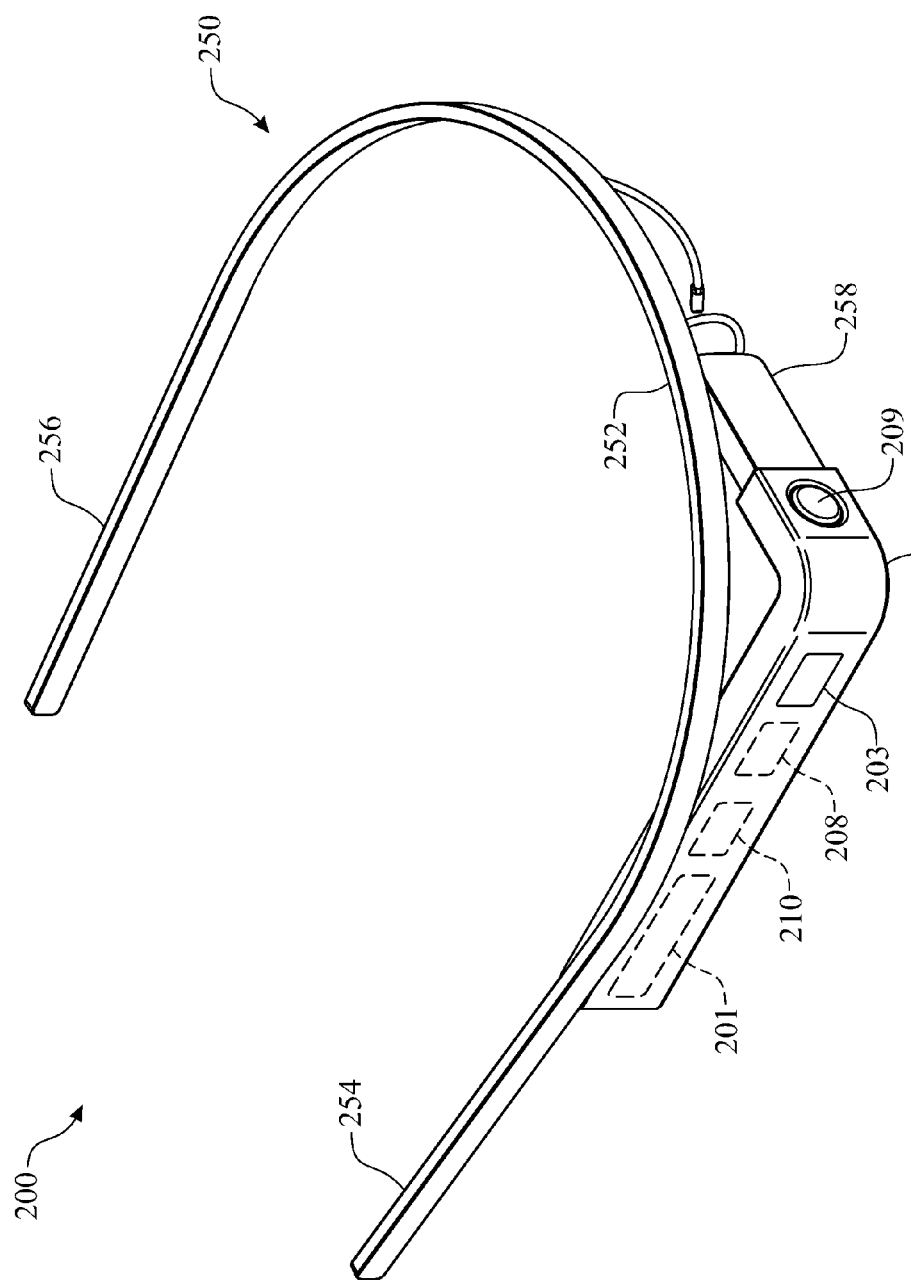
FIG. 12 presents an isometric view of a wearable computing device for receiving, transmitting, and displaying data, in accordance with an exemplary embodiment.
Figure 13:
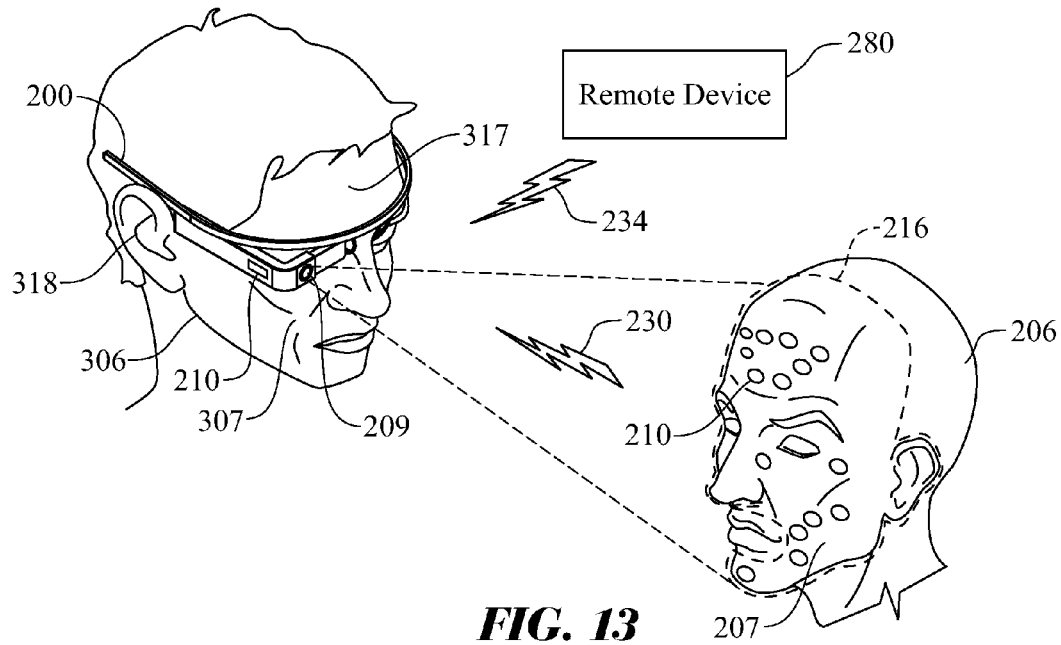
FIG. 13 presents an isometric view of an exemplary embodiment, showing the wearable computing device, originally introduced in FIG. 12, and illustrating facial movement being detected by sensors, received by the wearable computing device, and transmitted to a remote device via wireless communication.

Referring now primarily to FIGS. 12 and 13, an example wearable computing system 200 is presented. The system 200 is shown in the form of eyeglasses 250. The eyeglasses 250 include a lens element 258 and a frame 252 with side arms 254, 256 extending therefrom. A body 260 of the eyeglasses 250 can be attached to, affixed to, or integrated into the frame 252. The body 260 can be adapted as a computing system housing 260, for housing computing system components, such as a computer 201, a sensor 210, a projector 208, a camera 209, and a user interface, such as a finger-operable touch pad 203, as will be described in more detail below.

The frame 252 and extending side arms 254, 256 are configured to secure the eyeglasses 250 to a first user's face 307. When the eyeglasses 250 are worn by a first user 306, the frame 252 can rest on the first user's forehead 317. The side arms 254, 256 are each projections that extend outwardly, away from the lens element 258 and can be positioned behind the first user's ears 318 to secure the eyeglasses 250 to the user's face 307. The frame 252 and side arms 254, 256 can be formed of a solid rigid polymer, plastic, and/or metal structure, or can be formed as a hollow structure of similar material to allow for wiring and interconnection of internal electrical components throughout the eyeglasses 250.

Figure 14:
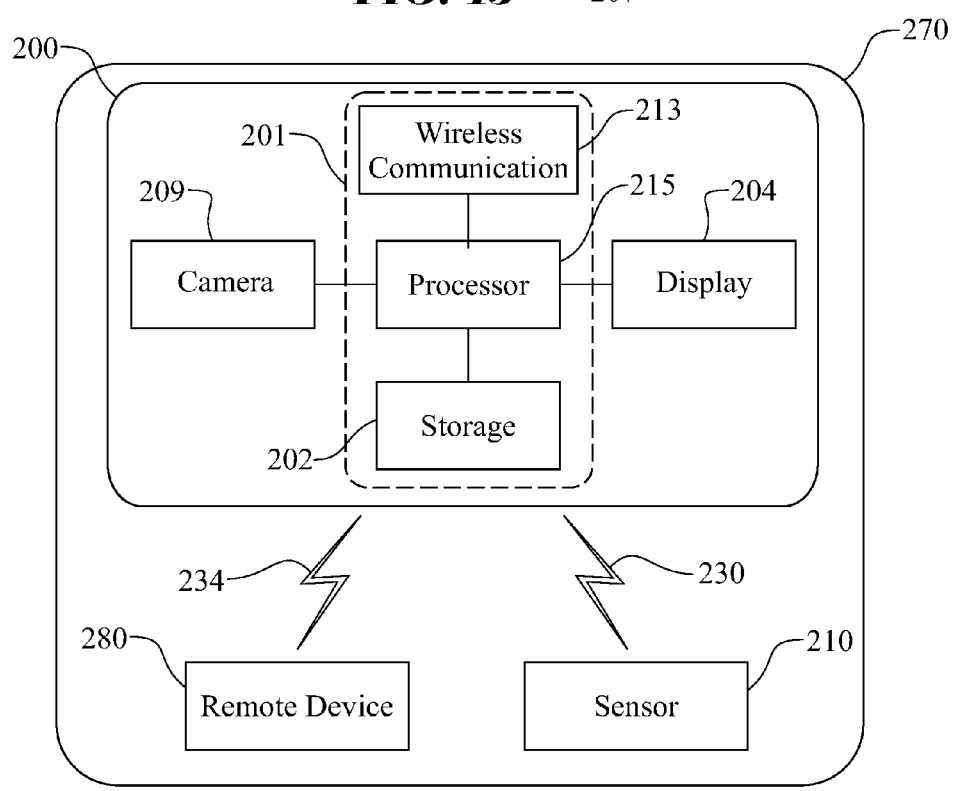
FIG. 14 presents a schematic diagram of a computer network infrastructure, in accordance with an exemplary embodiment.

As explained above, the system 200 can include on-board computing components, such as the computer 200, sensors 210, projector 208, camera 209, and the finger-operable touch pad 203. The on-board computing components are shown positioned within the housing 260 attached to the extending side arm 254 of the eyeglasses 250; however, it is understood that any one of or a multitude of the computing components may be provided on other parts of the eyeglasses 250 or can be remotely positioned, being in wireless or wired communication via a communication link 234 with the eyeglasses 250. The computer 201 can include a processor 215, memory, and/or storage 202, as illustrated in FIG. 14. The computer 201 can be configured to receive facial movement data from sensors 210 and/or the camera 209 and/or the computer 201 can be configured to receive user input commands associated with facial movement stimulation and measurement via the touch pad 203 and/or other user input devices, which data can be processed by the processor 215 and images generated for output onto the lens element 258.

Still referring primarily to FIGS. 12 and 13, the camera 209 is shown positioned on the front face of the body 260 of the eyeglasses 250; however, it is understood that the camera can be provided on other parts of the eyeglasses 250. The camera 209 is configured to capture still images as well as video. Although FIG. 12 illustrates a single camera 209, it is understood that more than one camera 209 can be included in the system 200. The camera 209 can face forward to capture still images and video of at least a portion of a real world view as perceived by the user 306 wearing the eyeglasses 250. Additionally, the camera 209, or a plurality of cameras (not shown), can be directed toward the user's face 307. The cameras 209 can be configured to capture still images and video of the user's face 307 in order to collect facial movement data of a wearer 306 over a predetermine amount of time to be stored and/or utilized by the wearable computing system 200 or other device 280 that is remotely located. A multitude of still images and/or video of the face 307 can be stored and compared by the computer 201 in order to produce a value corresponding to facial movement measurement of the user's face 307, as measured by the cameras 209.

The sensor 210 is shown positioned within the housing 260 attached to the extending side arm 254 of the eyeglasses 250; however, it is understood that the sensor 210 may be provided on other parts of the eyeglasses 250. Although FIG. 12 illustrates a single sensor 210, it is understood that more than one sensor 210 or a plurality of sensors 210 formed as an array of sensors 210 can be included in the system 200. The sensor 210 can be an electrode, accelerometer (as described above), or other sensor 210 well-known in the art. As described above with respect to the electrode and accelerometer, the sensor 210 (or electrode or accelerometer) can be adapted to provide electrical stimulation as well as to measure electrical nerve stimulation of the muscles of the face 307. The sensor 210 can be provided on the eyeglasses 250 to contact the first user's face 307 when worn, so as to be in electrically-conductive communication with the first user's 306 facial muscles. There are various anatomical facial zones that can contact the eyeglasses 250 when worn on the user's face 307, such as the glabellar, zygomatic, lateral canthal, and nasal zone, which are known in the art. An array of sensors 210 are preferably mounted on the eyeglasses 250 at locations corresponding to the zones, such that when eyeglasses 250 are worn by the user 306, the array of sensors 210 are in direct contact with the skin of the face 307, under which facial muscles lie within the zones (not shown).

Still referring primarily to FIGS. 12 and 13, the sensor 210 can also be located remotely with respect to the eyeglasses 250. For example, as best illustrated in FIG. 13, the sensor 210 can be attached to a second user's face 207, being in wired or wireless communication via a communication link 230 with the eyeglasses 250 secured to the first user's face 307. The sensors 210 can be directly attached to the second user's face 207 using a suitable adhesive or can be integrated into a flexible mask 216 adapted to conform to the features of the face 207. The flexible mask 216 may be separate from and remotely located with respect to the eyeglasses 250, as illustrated in FIG. 13, or the flexible mask 216 may be attached to or extend from the eyeglasses 250 (not shown). The first user 306 can be, for example, a physician attending to or monitoring the second user 206, who can be, for example, a facial paralysis patient requiring supervised facial muscle nerve stimulation and corresponding facial muscle measurement data collection.

The finger-operable touch pad 203 is shown mounted on the extending side arm 254 of the eyeglasses 250; however, it is understood that the touch pad 203 may be provided on other parts of the eyeglasses 250. The touch pad 203 can detect at least one of a position, pressure, and a movement of a finger via apparatuses and methods well-known in the art, such as capacitive sensing, resistance sensing, and the like. The touch pad 203 can facilitate user input. For example, the user 306 may tap the touch pad 203 with his or her finger to initiate facial electrical nerve stimulation via an array of electrodes 110 mounted on the eyeglasses 250 (not shown). The computer 201 may receive the finger tap input command, process the input, and command the electrode to generate an electrical impulse sufficient to stimulate facial muscle nerves. Additionally, other user input devices may be integrated into the system 200, such as a microphone, keyboard, and/or pointing devices (not shown).

The lens element 258 can be sufficiently transparent to allow the user 306 to see through the lens element 258, as is traditionally provided for non-computing eyeglasses. The lens element 258 may additionally act as a display element, which is normally provided with traditional computing systems. For example, the projector 206 can be coupled to an interior surface of the body 260 of the eyeglasses 250. The projector 206 can be configured to project an image 120 onto an exterior surface 259 (FIG. 15) of the lens element 258. The lens element 258 can also act as a light-projection system and can include a reflective coating, which reflects light projected onto the lens element 258 from the projector 206. Alternatively, the projector 206 can be a scanning laser device that interacts directly with the user's 306 retina. Although, FIG. 12 shows only one lens element 258 and one projector 208, it is understood that the system 200 may include two or more lens elements 258 and projectors 208. The lens elements 258 can include a transparent or semi-transparent display surface 259, such as a light emitting diode (LED) display, a liquid crystal display (LCD), and the like. It is understood that any display surface can be implemented, provided that it allows the eyeglass wearer 306 to view images displayed thereon.

Referring now primarily to FIG. 14, an example schematic diagram of a computer network infrastructure is illustrated. In an example network 270, a device, such as the wearable computing system 200, is adapted to communicate, via the communication link 230 (e.g. a wired or wireless connection), with the sensor 210, which may be an electrode, accelerometer, or other known sensor, as described with reference to FIGS. 12 and 13. Additionally, the wearable computing system 200 is adapted to communicate, via the communication link 234 (e.g. a wired or wireless connection), with a remote device 280.

Referring primarily to FIGS. 13 and 14, the sensor 210 can transmit an electrical impulse effective to contract a muscle in the user's face 207, 307 via the communication link 230. The sensor 210 can also detect and/or measure nerve-induced electrical stimulation of the muscle in the user's face 207, 307 and transmit the detected and/or measured data corresponding to the nerve-induced electrical stimulation to the computing system 200 via the communication link 230. The data can be stored in storage 202, processed by the processor 215, and the processed data displayed on a display 204 of the wearable computing system 200, as will be described below with reference to FIG. 15.

The system 200 includes the computer 201, having the processor 215, memory and/or non-volatile storage 202, and a wireless communication interface 213. The display 204 and camera 209 are connected to the computer 201. The processor 215 can be any type of processor, such as a microprocessor or a digital signal processor, for example. The processor 215 with supporting software can be adapted to transmit electrical impulses to the sensors 210, such as electrodes 110, through wiring or a wireless network 230, in such a pattern and with such intensity as to electrically stimulate and contract musculature in the face 307 and induce desired facial movements or expressions in the face 307. The processor 215 can also be adapted to receive and store electrical signals that correspond to voluntary and involuntary nerve-induced electrical stimulation of the musculature received by the sensors 210. The processor 215 can store such facial movement measurements in storage 202. Additionally, software, such as the software configured to process and utilize facial movement data, can be stored in storage 202.

The wireless communication interface 213 can include one or more network interface cards (NIC) that can provide the capability for the wearable computing system 200 to network with, for example, a personal area network (PAN), such as a Bluetooth® network, a local area network (LAN), such as a Wi-Fi network, or a wide area network (WAN), such as a cellular mobile communications network, for example. The communication links 230, 234 can be wired or wireless.

The remove device 280 can be another computing device, such as a personal computer 101 (FIG. 1), a laptop, a computer tablet, a cellular telephone, a handheld device, a video game console 141 (FIG. 5), or the like, that is configured to receive facial movement data from and transmit facial movement data to the wearable computing system 200 via the communication link 230.

Figure 15:
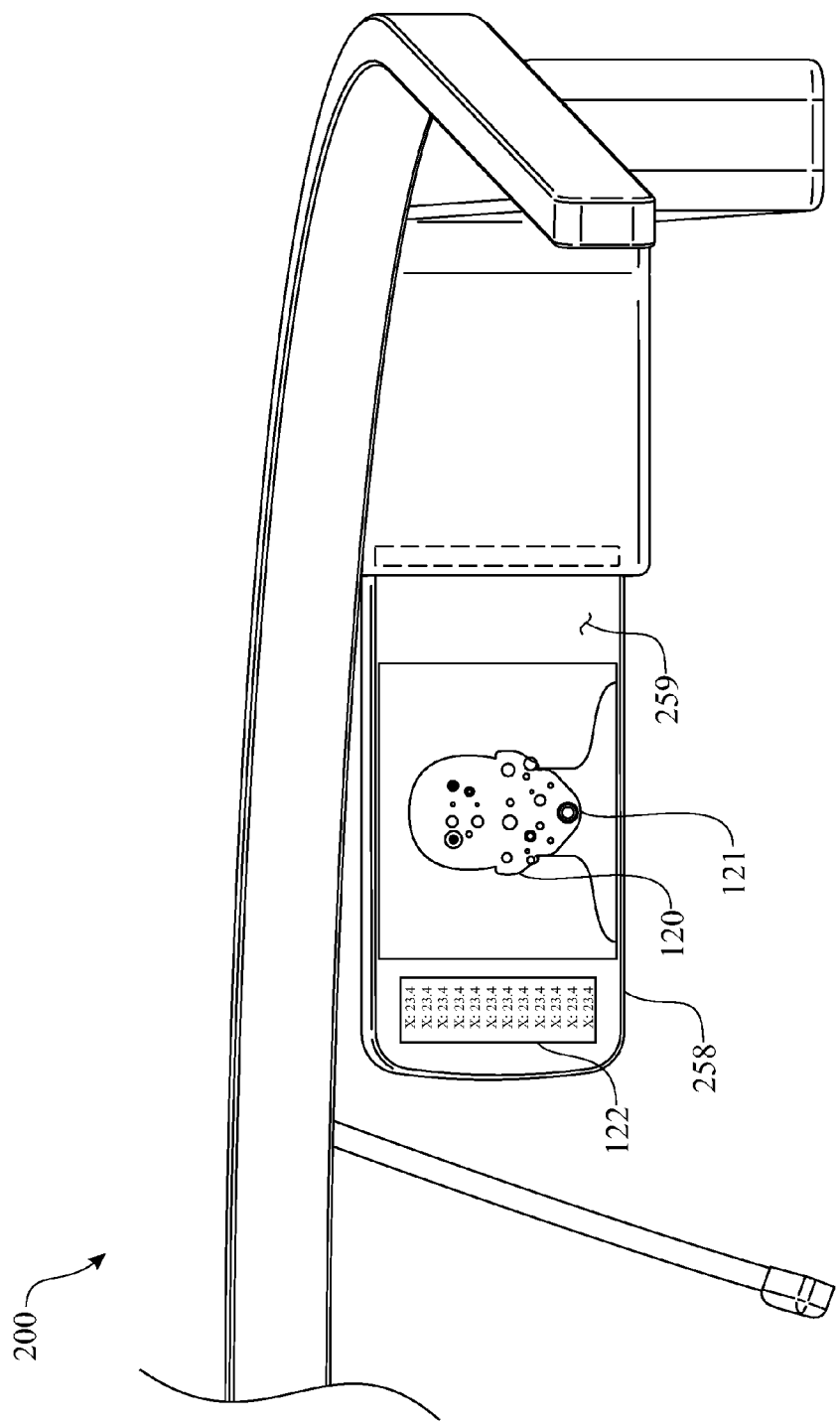
FIG. 15 presents an isometric front view of a display of the wearable computing device, originally introduced in FIG. 12, showing an image presented on the display, the image corresponding to facial movement data received by the wearable computing device.

An example provided image 120 being displayed on the exemplary display 258 is illustrated in FIG. 15. In particular, the example illustrates the facial image 120 including facial movement indications 121 described above with reference to FIG. 2 being displayed on the computer monitor 104, except that the image 120 is displayed on the display surface 259 of the display 258 of the wearable computing device 200 in FIG. 15, rather than the personal computer monitor 104 of FIG. 2. It is understood that facial movement data can also be displayed on the display 258 in other formats, such as a table 122 or spreadsheet format, for example, listing numerical data corresponding to facial movement output signals.

Figure 16:
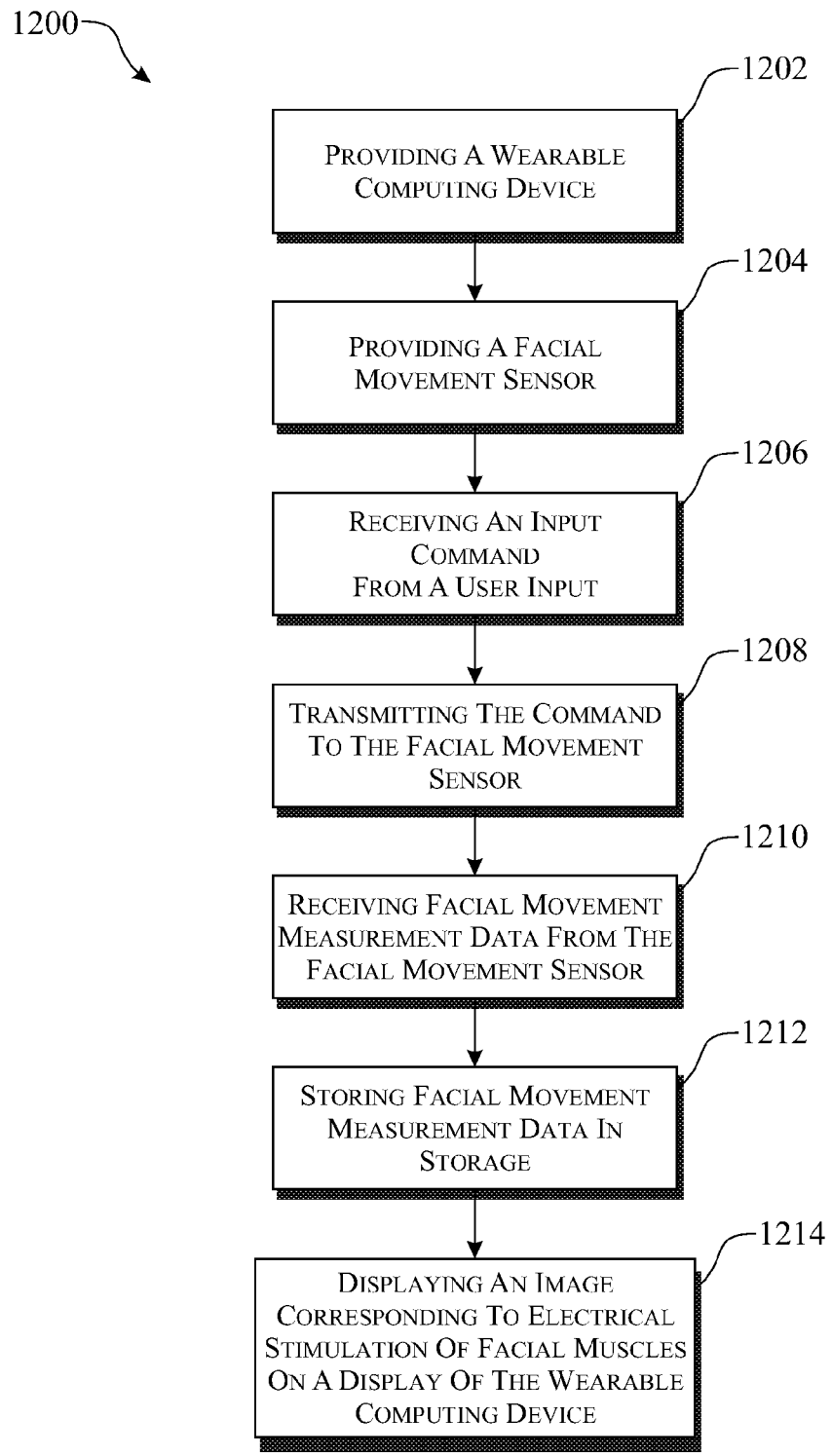
FIG. 16 presents a flow chart illustrating a method according to an exemplary embodiment in which facial movement data is received, stored, and displayed by a wearable computing device.
Figure 17:
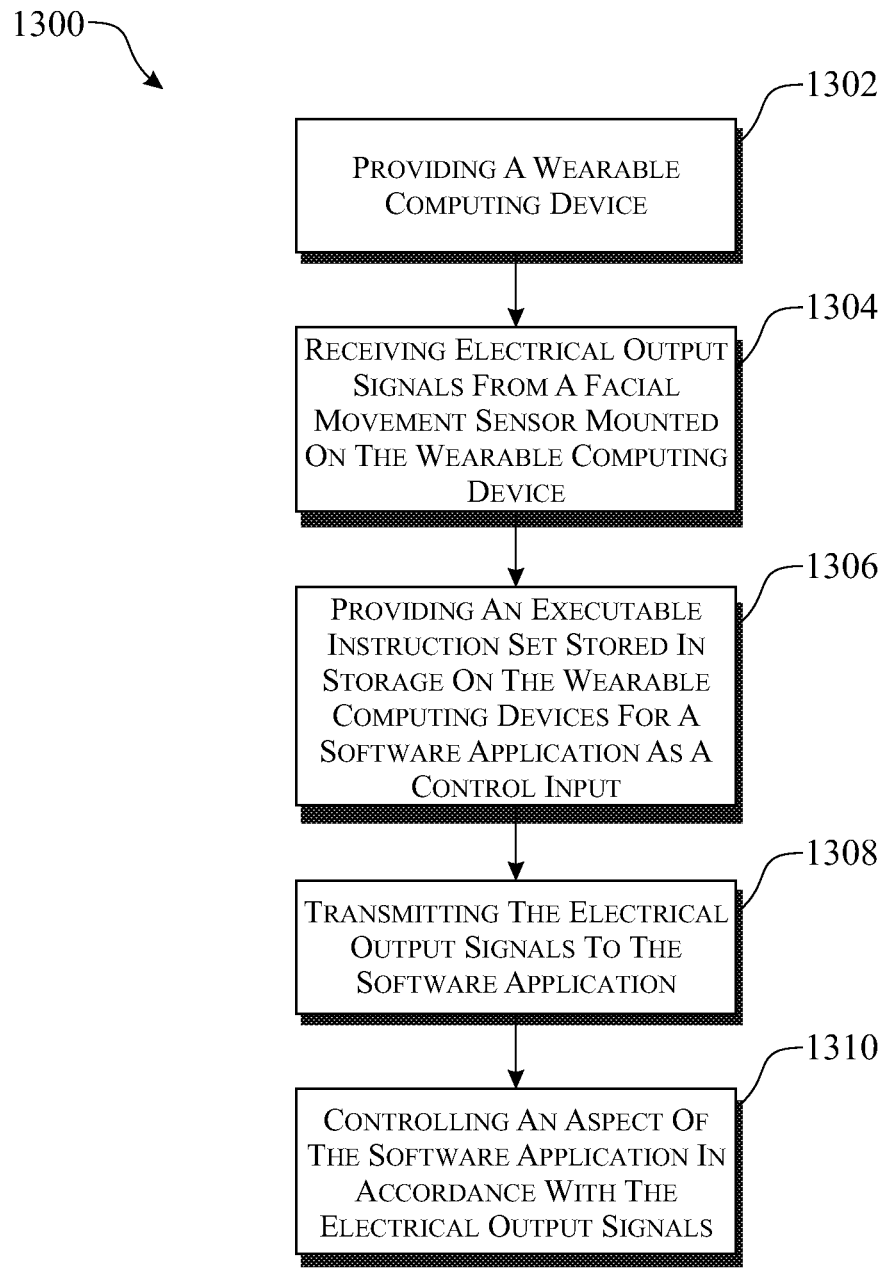
FIG. 17 presents a flow chart illustrating a method according to an exemplary embodiment in which facial movement data received by a wearable computing device is provided as a control input to a software application running on a remote device or the wearable computing device.

Exemplary methods involving a wearable computing system, such as 200, and stimulation and measurement of facial muscle movement utilizing the wearable computing system is presented in FIGS. 16 and 17. Although FIGS. 16-17 show a specific order of executing functional logic blocks, the order of executing the blocks may be changed relative to the order shown. Also, two or more blocks shown in succession may be executed concurrently or with partial concurrence. Certain blocks may also be omitted for the sake of brevity. And some blocks are merely exemplary steps in an exemplary implementation, but are not required in order to be in accordance with the present invention.

Referring now primarily to FIG. 16, a flow chart illustrating a method according to an exemplary embodiment in which facial movement data is received, stored, and displayed by the wearable computing device 200 is generally indicated by reference numeral 1200. More specifically, in block 1202, a wearable computing system is provided. The wearable computing system may be in the form of eyeglasses, a mask, contact lenses, and the like. In block 1204, a facial movement sensor, such as for example, an electrode, a camera, or an accelerometer is provided. In block 1206, the wearable computing system can receive an input command associated with commanding facial movement sensors that may be mounted on the wearable computing system or may be remotely located. The input command may be an input from a user input interface, such as a touch pad or microphone, and the command may be a command for the facial movement sensors to transmit an electrical impulse to provide facial movement stimulation to a user's facial muscles. In block 1208, based on the received input command, the wearable computing system transmits a command to facial movement sensors to provide facial movement stimulation to the user's facial muscles. In block 1210, the wearable computing system receives facial movement data from facial movement sensors, which data corresponds to nerve-induced electrical stimulation of facial muscles. The facial movement data can be received by a processor of the wearable computing system over a wired or wireless network. In block 1212, the wearable computing system stores facial movement data in non-volatile or non-transitory storage. In block 1214, the wearable computing system displays an image corresponding to nerve-induced electrical stimulation of facial muscles on a display of the wearable computing system.

Referring now primarily to FIG. 17, a flow chart illustrating a method according to an exemplary embodiment in which facial movement measurement data received by a wearable computing device is generally indicated by reference number 1300. More specifically, in block 1302, a wearable computing device is provided. The wearable computing device may be in the form of eyeglasses, a mask, contact lenses, and the like. In block 1304, the wearable computing device receives facial movement measurement data from facial movement sensors that may be mounted on the wearable computing device or may be remotely located with respect to the wearable computing device. The facial movement measurement data may be in the form of, for example, electrical output signals from an electrode, accelerometer or other sensor, corresponding to electrical stimulation of the facial muscles. Alternatively, the facial movement data may be muscular activity measured by a camera of the wearable computing device, as described above. In block 1306, an executable instruction set stored in non-volatile or non-transitory storage on the wearable computing device is provided. The instruction set can be a software application that is adapted to receive facial movement data as a control input. For example, the software application may be an executable instruction set for a video game adapted to utilize and command the output of the facial movement sensors (e.g. electrode, accelerometer, camera, etc.) to control one or more aspects or characters of the video game, as described above with reference to FIG. 5. For example, electrical impulses transferred from the video game software to electrodes to induce facial movement may correspond to facial movements or expressions, which are made by a character presented on the display associated with the video game. As another example, the output of the facial movement sensors may be utilized as an audio and/or visual component of the video game. In block 1308, the wearable computing device transmits the electrical output signals from the facial movement sensors to the software application as an input command. In block 1310, an aspect of the software application is controlled in accordance with the electrical output signals from the facial movement sensors.

It will be appreciated by those skilled in the art that the apparatus and method in the various embodiments described herein above have numerous potential applications beyond those which are expressly described herein. For example, the apparatus and method may be used to study the contagiousness of emotions or the effect which changing facial expressions have on emotions in human subjects. In some applications, the apparatus and method may be used in mood intervention scenarios in which facial expressions that are indicative of positive emotions are transferred from one subject to another subject. The apparatus and method may be used as a polygraph in which facial twitches and movements may indicate whether a subject is lying in response to questioning. In some embodiments, the apparatus may be constructed with non-magnetic parts for use in conjunction with an MRI or other medical device.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

What is claimed is:
1. A wearable computing system, comprising:
  eyeglasses, comprising:
    a lens element including a display,
    a frame with side arms extending therefrom, and an eyeglasses body adapted to function as a computing system housing, the computer system housing comprising a computer having a processor, storage, and a wireless communication device; and at least one sensor adapted to measure facial muscle movement in a user, the at least one sensor in electrical communication with the computer, wherein the at least one sensor is an electrode in electrically conductive communication with a facial muscle of the user and is adapted to transmit an electrical impulse to the facial muscle of the user to electrically stimulate the facial muscle.

2. The wearable computing system as recited in claim 1, wherein the at least one sensor is a camera having a camera lens, wherein the camera is mounted on the eyeglasses such that when the eyeglasses are worn by the user, the camera lens is directed toward the user's face and is configured to capture at least one of a still image and video of the face and wherein the processor is configured to receive and compare captured images and video and generate facial movement measurement data therefrom.

3. The wearable computing system as recited in claim 2, wherein the computer is adapted to output facial muscle movement signals indicative of facial muscle movement of the user to the display of the eyeglasses.

4. The wearable computing system as recited in claim 1, further comprising a mask, wherein the at least one electrode comprises a plurality of electrodes that are carried by the mask.

5. The wearable computing system as recited in claim 4, wherein the mask extends from the eyeglasses.

6. The wearable computing system as recited in claim 4, wherein the plurality of electrodes are located at each of a top portion, a middle portion, and a bottom portion of the face, wherein the top portion, corresponds to the user's forehead area, and wherein the middle portion corresponds to the user's eye and nose area, and wherein the bottom portion corresponds to the user's mouth area.

7. The wearable computing system as recited in claim 1, wherein the at least one electrode comprises a plurality of electrodes mounted on the eyeglasses such that when the eyeglasses are worn by the user, the plurality of electrodes are in electrically conductive communication with the user's facial muscles.

8. The wearable computing system as recited in claim 7, wherein the computer is adapted to output facial muscle movement signals indicative of facial muscle movement of the user to the display of the eyeglasses.

9. The wearable computing system as recited in claim 7, further comprising an instruction set stored in computer storage corresponding to video game software.

10. The wearable computing system as recited in claim 9, wherein the electrical impulse corresponds to a movement of a video game character presented on the display.

11. A method of measuring and indicating facial movement of a user, comprising steps of:

providing a wearable computing device having a processor, storage, a user input, and a display;

providing at least one facial movement sensor mounted on the wearable computing device such that the at least on facial movement sensor is directed toward the user's face when the wearable computing system is worn by the user;

receiving an input command from the user input commanding the at least one facial movement sensor to transmit an electrical impulse to provide facial movement stimulation to the user's facial muscles;

transmitting the command to the at least one facial movement sensor;

receiving facial movement measurement data from the at least one facial movement sensor, which data corresponds to nerve-induced electrical stimulation of the user's facial muscles;

storing facial movement measurement data in storage; and displaying an image corresponding to nerve-induced electrical stimulation of facial muscles on the display of the wearable computing device.

12. The method of measuring and indicating facial movement in a user as recited in claim 11, wherein the providing the wearable computing system comprises providing a wearable computing system in the form of one of a group of eyeglasses, a mask, and contact lenses.

13. The method of measuring and indicating facial movement in a user as recited in claim 12, wherein the providing at least one facial movement sensor comprises providing a camera having a camera lens directed toward the user's face.

14. The method of measuring and indicating facial movement in a user as recited in claim 13, further comprising:

the camera capturing at least one of a still image and video of the face, comparing captured images and video of the face, and generating facial movement measurement data therefrom.

15. The method of measuring and indicating facial movement in a user as recited in claim 12, wherein the providing at least one facial movement sensor comprises providing a plurality of electrodes in electrically conductive communication with facial muscles of the user.

16. The method of measuring and indicating facial movement in a user as recited in claim 15, further comprising transmitting an electrical impulse to facial muscles of the user to electrically stimulate the user's facial muscles.

* * * * *